United States Patent [19]

Erickson

[11] 4,293,609
[45] Oct. 6, 1981

[54] FLEXIBLE ABSORBENT LAMINATES

[75] Inventor: Robert E. Erickson, Midland, Mich.

[73] Assignee: The Dow Chemical Company, Midland, Mich.

[21] Appl. No.: 164,644

[22] Filed: Jun. 30, 1980

Related U.S. Application Data

[63] Continuation-in-part of Ser. No. 55,586, Jul. 9, 1979, abandoned.

[51] Int. Cl.³ .............................................. B32B 7/00
[52] U.S. Cl. ................................. 428/246; 128/284; 264/DIG. 47; 428/284; 428/286; 428/310; 428/511; 428/913
[58] Field of Search .................. 128/284, 286, 288; 428/246, 284, 286, 310, 511, 913; 264/DIG. 47

[56] References Cited

U.S. PATENT DOCUMENTS

| | | | |
|---|---|---|---|
| 3,669,822 | 6/1972 | Cowen | 428/507 |
| 3,670,731 | 6/1972 | Harmon | 128/284 |
| 3,888,256 | 6/1975 | Studinger | 128/287 |
| 3,890,974 | 6/1975 | Kozak | 128/287 |
| 4,076,673 | 2/1978 | Burkholder | 264/41 |
| 4,117,184 | 9/1978 | Erickson et al. | 428/913 |

Primary Examiner—James J. Bell
Attorney, Agent, or Firm—B. G. Colley

[57] ABSTRACT

Flexible absorbent laminates made from crushed films of lightly crosslinked or water-swellable hydrophilic polymers with layers of wicking substrates are disclosed. The crushed laminates are made by drying the laminates to less than 8% moisture and crushing them preferably between a yieldable roller and an enbossed roller. The crushed laminates have a tissue-like feel at low relative humidities with rapid absorption and are useful to make baby diapers or adult diapers.

28 Claims, 2 Drawing Figures

FLEXIBLE ABSORBENT LAMINATES

CROSS REFERENCE TO RELATED APPLICATION

This application is a continuation-in-part of Ser. No. 55,586, filed July 9, 1979 now abandoned.

BACKGROUND OF THE INVENTION

This invention relates to flexible absorbent laminates wherein a lightly crosslinked or water-swellable hydrophilic polymer film is bonded to wicking substrates, dried, and crushed to give laminate flexibility and high water absorption rates.

It is known from U.S. Pat. No. 3,669,822 dated June 13, 1972 that tissue/polyethylene film/tissue laminates can be crimped or embossed to give an improved hand or flexibility or tissue-like feel.

It is also known from French Pat. No. 2,375,985 dated Sept. 1, 1978 that non-woven fiber sheet/tissue/absorbent layer/tissue/polyethylene film laminates can be made flexible with adhesion to the film by adding an adhesive between the tissue and the polyethylene film followed by transverse creasing or crimping.

In U.S. Pat. Nos. 4,117,184 and 4,176,667, it is disclosed that tissue/aerated absorbent film/tissue laminates can be prepared.

While the laminates disclosed in U.S. Pat. No. 4,117,184 have good absorption rates for water, urine, and other body fluids or exudates they have a tendency to become brittle and inflexible in atmospheres of low relative humidity. The result is an unacceptable rattle sound when the laminate is flexed and the laminate has a stiff or board like feel.

SUMMARY OF THE INVENTION

It now has been found that laminates comprising a central crushed film of a lightly crosslinked or water-swellable hydrophilic polymer combined with wicking substrates can be prepared which are both highly absorbent and flexible at both high and low relative humidities.

The present invention is thus a flexible hydrophilic absorbent laminate which has a rapid absorption rate and is flexible at low and high relative humidities which comprises (a) a central, substantially discontinuous and crushed film consisting of a water-swellable hydrophilic polymer, and (b) a layer of wicking substrates bonded to both sides of said film.

While the absorbent film can be a solid film as in U.S. Pat. No. 4,076,673, dated Feb. 28, 1978, it is preferably an aerated film as disclosed in U.S. Pat. No. 4,117,184.

A further aspect of the present invention is a method of making the above laminates which comprises the steps of; reducing the moisture content of a laminate of a lightly crosslinked hydrophilic polymer film with wicking substrates to less than 8% by weight by passing said laminate through a drying zone, and passing said dried laminate through a crushing or cracking zone wherein said film is crushed into a plurality of pieces which remain substantially laminated to said substrates.

The laminates are useful to make absorbent articles such as baby diapers, adult diapers for incontinent patients, and the like since the laminates and/or articles readily absorb aqueous solutions such as blood, urine, and other body exudates. The absorbent articles contain one or more layers of wicking substrates such as non-woven fiber mats, tissue wadding, or cellulose fluff together with a water impermeable bottom sheet such as polyethylene and a water permeable top sheet such as a non-woven fiber mat.

BRIEF DESCRIPTION OF THE DRAWING

The drawing is a photographic reproduction of one species of the present invention.

DETAILED DESCRIPTION

Figure 1:
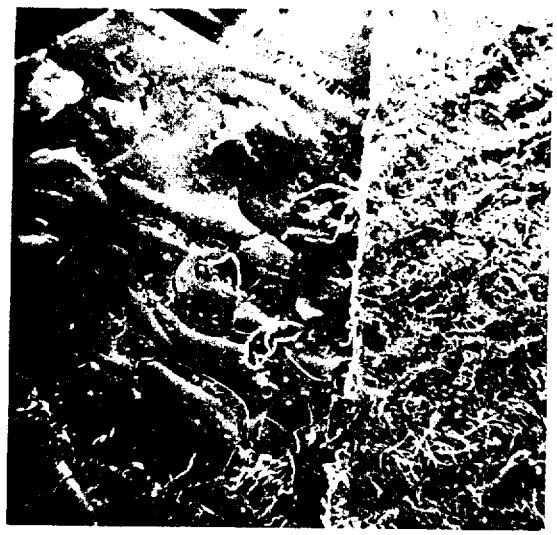
FIG. 1 shows a view taken with a scanning electron microscope of the laminate with the top layer of paper tissue fibers partially pulled back to expose the crushed film underneath. The bottom layer of paper tissue fibers is clearly evident beneath the crushed film.
Figure 2:
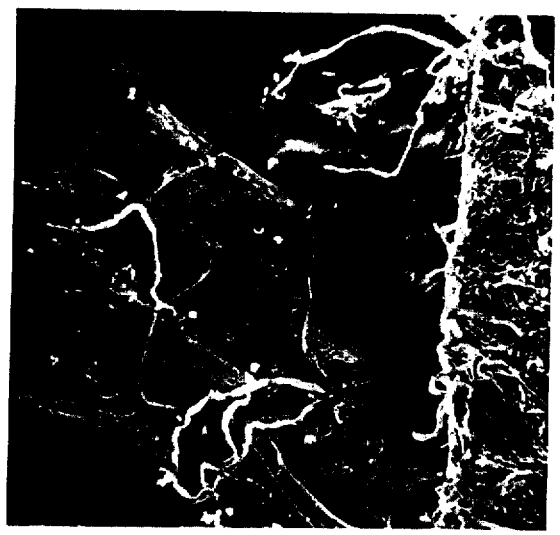
FIG. 2 is an enlarged view of the center portion of FIG. 1 showing in greater detail the craters and bubbles in the aerated film and the bonding of the film to the fibers.

The water-swellable or lightly crosslinked hydrophilic polymers useful in this invention can be any of the known hydrophilic polymers that are capable of being formed into a film. Examples of such polymers are disclosed in U.S. Pat. Nos. 3,997,484; 3,926,891; 3,935,099; 4,090,013; and 4,190,562.

The preferred hydrophilic polymers useful in this invention are polyelectrolytes and must be essentially water soluble in the salt form. Examples of useful polyelectrolytes include ammonium or alkali metal salts of homopolymers of acrylic or methacrylic acid and copolymers with one or more ethylenically unsaturated comonomers.

Preferably the polyelectrolyte is a partially saponified polyacrylate polymer. The polymer before saponification is the result of reacting together a mixture of monomers which comprises (1) 30 to 92 percent by weight of an alkyl acrylate wherein the alkyl group has from 1 to 10 carbon atoms, an alkyl methacrylate wherein the alkyl group has from 4 to 10 carbon atoms, or mixtures thereof; (2) 8 to 70 percent by weight of an olefinically unsaturated carboxylic acid; and (3) 0 to 15 percent by weight of an omega hydroxyalkyl acrylate wherein the hydroxyalkyl groups has from 1 to 4 carbon atoms.

Examples of useful alkyl acrylates include methyl acrylate, ethyl acrylate, propyl acrylate, butyl acrylate, and hexyl acrylate. Examples of useful alkyl methacrylates include methyl methacrylate, ethyl methacrylate, hexyl methacrylate, octyl methacrylate and decyl methacrylate. Examples of useful omega hydroxyalkyl acrylates include 2-hydroxyethyl acrylate, hydroxymethyl acrylate, 3-hydroxypropyl acrylate and 4-hydroxybutyl acrylate.

The olefinically unsaturated carboxylic acids useful in this invention are mono or polycarboxylic acids. Examples of monocarboxylic acids include acrylic acid, methacrylic acid, crotonic acid, and isocrotonic acid. Examples of polycarboxylic acids include maleic acid, fumaric acid, and itaconic acid.

The foregoing polyacrylates are then dissolved in an aqueous alkali metal hydroxide solution. The amount of hydroxide solution employed is sufficient to saponify some of the acrylate esters to alkali metal carboxylates and to neutralize the carboxylic groups of the polyacrylate to alkali metal carboxylates so that the saponified polyacrylate polymer has from 30 to 70 weight percent alkali metal carboxylates.

The partially saponified polyacrylate polymer is employed as a solution containing from 5 to 60 percent by weight of the polymer.

A list of applicable polymers which could be prepared from readily available monomers and converted into their salt form is as follows:
- acrylic acid—acrylate copolymers
- acrylic acid—acrylamide copolymers
- acrylic acid—olefinic copolymers polyacrylic acid
- acrylic acid—vinyl aromatic copolymers
- acrylic acid—styrene sulfonic acid copolymers
- acrylic acid—vinyl ether copolymers
- acrylic acid—vinyl acetate copolymers
- acrylic acid—vinyl alcohol copolymers and copolymers of methacrylic acid with all the above comonomers.

Illustrative examples of the polyfunctional crosslinking agents useful in this to convert the above polyelectrolytes into water-swellable polymers invention are set forth in U.S. Pat. Nos. 2,926,154; 3,224,986; and 3,332,901. These polyfunctional crosslinking agents are generally known as polyamide-polyamine epichlorohydrin adducts. The disclosures of these references are incorporated herein by reference. Similar crosslinking agents are also commercially available from Hercules Incorporated as Kymene 557 and Polycup 172. The structure of these adducts has been discussed in an article by M. E. Corr, et al Journal of Applied Polymer Science, Vol. 17, pages 721–735 (1973).

Illustrative examples of the difunctional agents useful in this invention are polyhaloalkanols such as 1,3-dichloroisopropanol; 1,3-dibromoisopropanol; sulfonium zwitterions such as the tetrahydrothiophene adduct of novolac resins; haloepoxyalkanes such as epichlorohydrin, epibromohydrin, 2-methyl epichlorohydrin and epiiodohydrin; polyglycidyl ethers such as 1,4-butanediol diglycidyl ether, glycerine-1,3-diglycidyl ether, ethylene glycol diglycidyl ether, propylene glycol diglycidyl ether, diethylene glycol diglycidyl ether, neopentyl glycol diglycidyl ether, polypropylene glycol diglycidyl ethers having an epoxy equivalent weight range from about 175 to about 380, bisphenol A-epichlorohydrin epoxy resins having an epoxy equivalent weight range from about 182 to about 975 and mixtures of the foregoing.

Also useful as crosslinking agents are monomeric amine-epihalohydrin adducts prepared by reacting at least two moles of an epihalohydrin with one mole of various monoamines, diamines and triamines at a temperature in the range from 0° to 90° C. for a time period of 0.5 to 8 hours. The reaction is carried out in a reaction media containing 20 to 90 percent water, lower alcohols such as methanol or ethanol, or in aqueous solutions of the lower alcohols. The amine-epihalohydrin adducts are used directly as made without separation or concentration. The preparation and use of amino-epihalohydrin adducts as crosslinking agents is further disclosed in the patent application by J. R. Gross, Ser. No. 796,627 filed May 13, 1977. This application is incorporated by reference herein.

Sulfonium zwitterions are known from U.S. Pat. Nos. 3,660,431, 3,749,737, and 3,749,738. The disclosures of these patents are incorporated herein by reference.

These crosslinking agents are used in an amount from about 0.05 to about 5.0% based on the weight of the polyelectrolyte used. This is generally sufficient to cause the polyelectrolyte to become lightly crosslinked.

It is sometimes desirable to add a small amount of an surfactant to the polyelectrolyte composition to aid in flowing on and removing the continuous film from the water impervious substrate. A secondary benefit of using a surfactant is to increase the wettability of the final dry absorbent film. Either anionic or nonionic surfactants may be used. Examples of the useful surfactants are the sodium alkyl sulfonates and the ethylene oxide derivatives of alkylated phenols and the like.

For the purpose of this invention, a moisture absorbent or water swellable polyelectrolyte or polymer is defined as one which absorbs greater than about 15 times its weight of synthetic or natural urine. Preferably the absorbency should be in the range from about 30–60 gram of urine per gram of polyelectrolyte or in the range of 90–250 grams of deionized water per gram of polyelectrolyte. The level of crosslinking agent used is a variable factor which is dependent upon the particular polyelectrolyte used and the molecular weight of the polyelectrolyte. Preferably, the amount used varies from the 0.25 to 3.0 percent based on the weight of the polyelectrolyte. However, this range is varied for each polyelectrolyte in order to adjust the absorbency of the final crosslinked material.

The water swellable laminates of this invention may be combined into absorbent pads with wicking or non-wicking substrates. Examples of wicking substrates include woven fabrics, non-woven fiber mats, cellulose fluff, polymeric foams, tissue paper, crepe paper, paper wadding, and paper toweling.

The flexible laminates of this invention are made by first reducing the moisture content of the aerated laminates prepared by U.S. Pat. No. 4,117,184 in a drying zone. It is to be understood that similar flexible laminates can be made using the non-aerated laminates or films of U.S. Pat. No. 4,076,673 and other hydrophilic polymers are set forth above.

The moisture content of the laminates must be reduced from their normal content of about 14% moisture to less than 8% and preferably in the range from 1–6%. If the moisture content is greater than about 8%, there is substantially no crushing or shattering of the film in the subsequent cracking zone since the film remains flexible. If the moisture content is less than 1% moisture, there is substantial tearing or rupturing of the wicking substrates such as the fibers of the paper tissue mats.

The above drying step can be accomplished with conventional drying equipment such as a steam heated drying drum, microwave heaters, infrared heaters, or similar equipment.

The second step of the process involves passing the dried laminate through a crushing or cracking zone wherein the film breaks into a plurality of pieces which remain substantially bonded to the substrates. This can be accomplished by passing the dried laminate together with a wire mesh screen through a pair of rollers where one of the rollers should have a yieldable or flexible surface. Suitable rollers are commercially available. They have an elastomeric surface with a Durometic A hardness from about 40 to about 100 and preferably in the range from 50 to 70. Generally these rollers are made from synthetic rubber such as neoprene, but other elastomers such as polyvinyl chloride, polyurethane, and the like surfaces are acceptable provided that they have the required Durometer hardness.

A preferred method is to use a yieldable roller coacting with a second steel roller having an engraved or etched pattern on the surface thereof.

The choice of the pattern is not critical as long as it has sufficient highs and lows to give a patterned imprint to the laminate. It is to be noted that merely embossing the laminate does not improve its hand and/or absorption. There must be a substantial amount of film breakage.

There are several variables in the crushing zone which must be considered in order to obtain an acceptable product. The degree of moisture in the laminate, the degree of pressure between the rolls, and the relative hardness of the yieldable roll are all interrelated. For example, if the yieldable roll is too soft and the pressure is too great, there will be substantial amounts of tearing of the substrates. At the other extreme with a relatively hard yieldable roll and little pressure, there will be little or no film crushing and hence little or no flexibility in the final laminates.

By suitable adjustments in the foregoing variables, one can obtain a sufficient crushing of the film within the laminate without tearing or destroying the wicking substrates which are bonded to the film.

The following examples are presented to further illustrate but not limit the invention.

EXAMPLES 1-3

Various samples of a tissue paper/aerated film/tissue paper laminate having the dimensions 3×12 inches and prepared by the method set forth in Example 9 of U.S. Pat. No. 4,117,184 were dried on a steam heated drum roll at 230°-240° F. for varying lengths of time. The samples each had a moisture content of 8-13% by weight prior to drying. Each sample was then combined with a 16 mesh stainless steel wire mesh and run through a pair of calender rolls at a rate of twenty feet per minute with a guage pressure of 40-50 psi. The upper roll was a 3 inch diameter by an 18 inch long steel roll with a synthetic rubber surface ¼ inch deep and having a 78 to 80 Shore A Durometer hardness. The lower roll was a relatively smooth steel roll of 5 inches diameter by 18 inches long.

The samples were then compared and observed for their softness or hand at 30-40% relative humidity on an arbitary scale of 1 to 10 where 1 represents the high stiffness of writing paper and the loud rattle of cellophane and 10 represents the low stiffness and the soft rustle of facial tissue paper. Any rating of 7 or more is considered satisfactory.

The results are set forth in Table I below:

TABLE I

| Experiment | Contact with Hot Drum (Seconds) | Percent Moisture in Dried Laminate | Softness Rating |
|---|---|---|---|
| Control 1 | 0 | 10-13 | 3 |
| Control 2 | 0 | 8-9 | 5 |
| Example 1 | 3 | 6 | 7 |
| Example 2 | 5 | 4 | 9 |
| Example 3 | 15 | <1 | 9 |

EXAMPLES 4-7

Following the procedure set forth in Example 2, the wire screen was replaced with screens having a variety of mesh sizes. The results are set forth in Table II.

TABLE II

| Example | Mesh | Screen Type Wire Dia. Inches | Percent Moisture in Dried Laminate | Rating |
|---|---|---|---|---|
| 4 | 25 | .014 | 4 | 8 |
| 5 | 16 | .023 | 4 | 9 |
| 6 | 12 | .041 | 4 | 8 |
| 7 | 8 | .025 | 4 | 8 |

EXAMPLES 8-10

A roll of paper/aerated film/paper laminate was prepared according to U.S. Pat. No. 4,117,184 and had the following characteristics: total weight 7.1 grams per square feet; paper tissue weight 3.3 grams/ft.$^2$; film weight 3.8 grams/ft.$^2$; film moisture content 14 percent.

The laminate was unwound from the feed roll and dried on a steam heated rotating drum having a surface temperature of 220°-230° F. and with variable speed and take off times so as to obtain variable drying times.

The laminate was immediately fed at 20 feet per minute to a pair of calender rolls having a guage pressure of 40-50 psi as in Example 1 except that the lower roll was tightly covered with a cylindrical cloth screen of 16 mesh with 0.023 inch diameter wires. The results are set forth in Table III.

TABLE III

| Example | Drum RPM | Laminate Contact Time Sec. | Dried Laminate Percent Moisture | Softness Rating |
|---|---|---|---|---|
| 8 | 9 | 19 | 3.6 | 9 |
| 9 | 15 | 15 | 4.3 | 9 |
| 10 | 15 | 12 | 5.5 | 8 |
| Control 3 | 15 | 10 | 8.0 | 5 |
| Control 4 | | (no drying) | 14.0 | 3 |

The above examples were tested for their absorption rate by the following test:

A sample of the laminate on a glass plate was placed under a 6×6 inch square metal box having ¼ inch thick walls. The box was weighted with lead weights on each corner to prevent leakage. Since the capacity of film to absorb water in the laminate (grams of saline solution per gram of film) and the weight of the film per square foot is known, it can be calculated what the capacity of the laminate sample will be. The saline solution used is 1% sodium chloride in water to simulate urine.

Into this box is poured 75% of the capacity of sample and a timer is started. When the liquid is absorbed completely as shown by lack of gloss due to free liquid, the timer is stopped. The time in seconds is the absorption rate.

The test results are given in Table IV.

TABLE IV

| Examples | Laminate Treatment | Absorption Rate (Seconds) |
|---|---|---|
| Control 4 | none | 1300 |
| Example 8 | crushed | 75-80 |
| Example 9 | crushed | 80-90 |
| Example 10 | crushed | 80-90 |

EXAMPLE 11

A laminate similar to Example 8 was prepared having the following characteristics: total weight 6.3 grams per square feet, tissue weight, 2.6 grams per ft.$^2$ film weight, 3.7 grams per ft.$^2$ and 13–15 percent moisture.

This laminate was dried to 4% moisture and crushed as set forth in Example 8 at a nip pressure of 40–50 psig. The flexible crushed laminate had a softness rating of 7.

EXAMPLE 12

The procedure of Example 11 was repeated using a gauge pressure of 75 psi. The resulting flexible cracked laminate had an increased softness rating of 9.

EXAMPLE 13

The procedure of Example 9 was repeated using microwave heating and radiant (infra red) heating in place of the steam heated drum. The same softness rating was obtained.

EXAMPLE 14

An absorbent laminate containing a film weight of 3 grams/ft.$^2$ and a tissue weight of 2.8 grams/ft.$^2$ (1.4 grams/ft.$^2$ on each side) was prepared as described in Examples 9 and 10 of U.S. Pat. No. 4,117,184. The tissue was removed from one side of a large sample of the film and placed on the surface of a laboratory table. Deionized water was "mist" sprayed on the surface of the film and a fibrous, non-woven fabric with a weight of 8.37 g/ft.$^2$ (Scott "Hi-Loft") was placed on the tacky surface and pressed firmly with a hand rubber roll. After conditioning for one week at 72° F. and 50% relative humidity, a sample of the laminate was dried to 4% moisture content. The dry laminate was placed on a screen (16 mesh, 0.023" dia wire) and run between a rubber covered steel roll (78 Durometer A hardness) and a steel roll at a gauge pressure of approximately 50 psig. The laminate had a softness rating of about 8–9.

Control 5

An absorbent film/tissue laminate was made by the technique described in Examples 9 and 10 of U.S. Pat. No. 4,117,184. The weight of the laminate was approximately 6.5 grams/ft.$^2$ with an absorbent film weight of 3.7 grams/ft.$^2$ and a total tissue weight of 2.8 grams/ft.$^2$ (1.4 grams/ft.$^2$ on each side of the film). The laminate had about 14% moisture by weight.

The laminate was cut into 3 inch wide strips about 12 inches long. A strip of laminate was run between two matched, engraved steel rolls under 40 psig gauge pressure at 20 feet per minute. The pattern was perfectly reproduced in the laminate but the flexibility of the laminate was not increased as evidenced by visual observation. Two different, deeply engraved patterns were used with no evidence of increased flexiblity in the laminate. This illustrates the fact that with a high moisture content laminate, there is no crushing of the film because the film remains flexible and does not break.

Control 6

The laminate described in Control 5 is run between a rubber covered steel roll (rubber hardness of about 50–60 Durometer A) and a 2-inch wide engraved pattern roll. Sufficient pressure was used to transfer the engraved roll pattern into the laminate. The flexibility of the laminate was not significantly increased by this action. Ten different engraved pattern rolls were tested with no significant improvement noted in flexibility.

EXAMPLE 15

The laminate described in Control 5 was placed on a fibrous belt that was heated from the underside by an infrared heating bar to a temperature of about 160°–180° F. The laminate was exposed to the heated belt for about 20–30 seconds to reduce the moisture content and immediately run between the rolls described in Control 6. The engraved roll pattern was transferred to the laminate and the flexibility of the laminate was significantly increased. The laminate was soft and pliable with a hand similar to paper tissue.

EXAMPLE 16

Five engraved roll patterns were selected and tested according to Example 15. All of the patterns produced a significant increase in the flexibility of the laminate when the laminate was preheated and dried prior to running between the rolls.

EXAMPLE 17

An absorbent composition was made as follows:

|  | Parts by wt. (dry) | Parts by Wt. (wet) |
|---|---|---|
| Acrylic Polymer Solution* | 94.4 | 374.6 |
| Polyoxyethylene Sobitan monolaurate | 5.0 | 5.0 |
| Polyamine/Epichlorohydrin resin** | 0.6 | 14.4 |
| Deionized water to reach 20% solids | — | 106.0 |

*Made according to Example 1 of U.S. Pat. No. 4,076,673.
**Kymene 557.

A glass plate (6×18 inches) was precoated with a hard surface silicone release coating resin. The plate was preheated to 250° F. in a forced hot air oven (oven temperature of 250° F.) and a 15 mil wet film of the absorbent composition was cast on the hot, release coated, glass plate and placed in the hot air oven for 1 minute. The plate was removed from the oven, the film lifted from the plate, and placed in a 50% relative humidity, 72° F. controlled room for 24 hours.

The film was placed on a large glass plate and sprayed with a light mist of deionized water to make the surface tacky. A piece of woven cotton textile (65×65 count) was immediately placed on the surface of the absorbent film and pressed firmly in position with a hard rubber roll. The one sided laminate was placed with the film side up and a second piece of the cotton textile was adhered to the film surface as previously described.

The absorbent laminate was placed in a controlled environment (75° F., 50% RH) for 24 hours and then dried in a 200° F. oven to a moisture content of approximately 3 percent. The laminate was placed on a wire screen (16 mesh, 0.023" wire) and run between a rubber covered steel roll (Rubber hardness of 78 Durometer A) and a steel roll at a gauge pressure of approximately 40 psi and roll speed of 20 ft./minute. The laminate flexibility was greatly increased. Originally it was stiff and boardy and after calendering, it is soft and pliable.

EXAMPLE 18

An absorbent film was obtained as described in Example 17. A piece of ⅛ inch thick, flexible, open cell urethane foam of about 1.5 to 2.0 lbs/ft.$^3$ density was laminated to each surface of the film by the method described in Example 17. After 24 hours aging the moisture content of the laminate was reduced to about 2–3% by drying and the dry laminate was run between the calender rolls as described. The mechanical operation significantly increased the flexibility of the laminate from a rather stiff material to a soft flexible material.

I claim:

1. A flexible hydrophilic absorbent laminate which has a rapid absorption rate and is soft and flexible at low and high relative humidities which comprises
   (a) a central, substantially discontinuous and crushed film consisting of a water-swellable hydrophilic polymer, and
   (b) a layer of wicking substrates bonded to both sides of said film.

2. The laminate of claim 1 wherein the film comprises an aerated film having a density ranging from about 1.1 to 0.3 grams per cubic centimeter.

3. The laminate of claim 1 wherein the wicking substrates on the top or bottom are selected from the group consisting of woven fabrics, paper tissues, nonwoven fiber mats and polymeric foams.

4. An absorbent pad which comprises the absorbent laminate of claim 1, one or more layers of wicking substrates, a water impermeable bottom sheet and a water permeable face sheet.

5. The absorbent pad of claim 4 wherein said water impermeable bottom sheet is polyethylene and said face sheet is a non-woven fiber mat.

6. A flexible hydrophilic absorbent laminate which has a rapid absorption rate and is soft and flexible at low and high relative humidities which comprises
   (a) a central, substantially discontinuous and crushed film consisting of a lightly crosslinked carboxylic polyelectrolyte, and
   (b) a layer of wicking substrates bonded to both sides of said film.

7. The laminate of claim 6 wherein the film comprises an aerated film having a density ranging from about 1.1 to 0.3 grams per cubic centimeter.

8. The laminate of claim 6 wherein the wicking substrates on the top or bottom are selected from the group consisting of woven fabrics, paper tissues, non-woven fibers mats and polymeric foams.

9. An absorbent pad which comprises the absorbent laminate of claim 6, one or more layers of wicking substrates, a water impermeable bottom sheet and a water permeable face sheet.

10. The absorbent pad of claim 9 wherein said water impermeable bottom sheet is polyethylene and said face sheet is a non-woven fiber mat.

11. A hydrophilic absorbent laminate which has a rapid absorption rate and is soft and flexible at low and high relative humidities which comprises
    (a) a central, substantially discontinuous, cracked and aerated film having a density from about 1.1 to 0.3 grams per cubic centimeter and consisting of a lightly crosslinked carboxylic polyelectrolyte, and
    (b) a layer of wicking substrates bonded to both sides of said film wherein said substrates on the top or bottom are the same or different and are selected from the group consisting of woven fabrics, paper tissues, non-woven fiber mats and polymeric foams.

12. The laminate of claim 11 wherein said substrates are woven fabrics.

13. The laminate of claim 11 wherein said substrates are non-woven fiber mats.

14. The laminate of claim 11 wherein said substrates are paper tissues.

15. The laminate of claim 11 wherein said substrates are polymeric foams.

16. The laminate of claim 15 wherein said polymeric foams are polyurethane foams.

17. A process for making the flexible laminate of claim 1 which comprises
    (a) reducing the moisture content of a laminate of a water-swellable hydrophilic polymer film with wicking substrates to less than 8% by weight by passing said laminate through a drying zone, and
    (b) passing said dried laminate through a crushing zone wherein said film breaks into a plurality of pieces which remain essentially laminated to said substrates.

18. A process for making the flexible laminate of claim 1 which comprises
    (a) reducing the moisture content of a laminate of a water-swellable hydrophilic polymer film with wicking substrates to less than 8% by weight by passing said laminate through a drying zone, and
    (b) passing said laminate through a cracking zone having a first roller with a yieldable surface coacting with a second roller with a predetermined patterned surface whereby said laminate is squeezed between said rollers with sufficient pressure to crack said film substantially completely into a plurality of pieces with a minimum amount of tearing of said substrates.

19. The process of claim 18 wherein said laminate moisture content is in the range from 1 to 6%.

20. The process as set forth in claim 18 wherein said first roller has an elastomeric surface wherein the elastomer has a Durometer A hardness from about 40 to about 100.

21. The process as set forth in claim 20 wherein said first roller is made from a synthetic rubber.

22. The process as set forth in claim 18 wherein said second roller is made from steel with an engraved surface pattern.

23. A process for making the flexible laminate of claim 6 which comprises
    (a) reducing the moisture content of a laminate of a lightly crosslinked polyelectrolyte film with wicking substrates to less than 8% by weight by passing said laminate through a drying zone, and
    (b) passing said dried laminate through a crushing zone wherein said film breaks into a plurality of pieces which remain essentially laminated to said substrates.

24. A process for making the flexible laminate of claim 6 which comprises
    (a) reducing the moisture content of a laminate of a lightly crosslinked polyelectrolyte film with wicking substrates to less than 8% by weight by passing said laminate through a drying zone, and
    (b) passing said laminate through a cracking zone having a first roller with a yieldable surface coacting with a second roller with a predetermined patterned surface whereby said laminate is squeezed between said rollers with sufficient pressure to crack said film substantially completely into a plurality of pieces with a minimum amount of tearing of said substrates.

25. The process of claim 24 wherein said laminate moisture content is in the range from 1 to 6%.

26. The process as set forth in claim 24 wherein said first roller has an elastomeric surface wherein the elastomer has a Durometer A hardness from about 40 to about 100.

27. The process as set forth in claim 26 wherein said first roller is made from a synthetic rubber.

28. The process as set forth in claim 24 wherein said second roller is made from steel with an engraved surface pattern.

* * * * *